(12) United States Patent
Dickerman

(10) Patent No.: US 11,998,519 B2
(45) Date of Patent: Jun. 4, 2024

(54) COMPOSITIONS AND METHODS FOR PREVENTION AND REDUCTION OF TRAUMATIC BRAIN INJURY

(71) Applicant: Rob D. Dickerman, Frisco, TX (US)

(72) Inventor: Rob D. Dickerman, Frisco, TX (US)

( * ) Notice: Subject to any disclaimer, the term of this patent is extended or adjusted under 35 U.S.C. 154(b) by 132 days.

(21) Appl. No.: 17/696,723

(22) Filed: Mar. 16, 2022

(65) Prior Publication Data

US 2022/0218642 A1      Jul. 14, 2022

Related U.S. Application Data

(63) Continuation of application No. 17/572,368, filed on Jan. 10, 2022, now abandoned.

(60) Provisional application No. 63/137,507, filed on Jan. 14, 2021.

(51) Int. Cl.
| | |
|---|---|
| *A61K 31/198* | (2006.01) |
| *A61K 31/197* | (2006.01) |
| *A61K 31/375* | (2006.01) |
| *A61K 31/4188* | (2006.01) |
| *A61K 31/4415* | (2006.01) |
| *A61K 31/455* | (2006.01) |
| *A61K 31/519* | (2006.01) |
| *A61K 31/714* | (2006.01) |

(52) U.S. Cl.
CPC .......... *A61K 31/198* (2013.01); *A61K 31/197* (2013.01); *A61K 31/375* (2013.01); *A61K 31/4188* (2013.01); *A61K 31/4415* (2013.01); *A61K 31/455* (2013.01); *A61K 31/519* (2013.01); *A61K 31/714* (2013.01)

(58) Field of Classification Search
None
See application file for complete search history.

(56) References Cited

U.S. PATENT DOCUMENTS

| | | |
|---|---|---|
| 4,687,782 A | 8/1987 | Brantman |
| 5,306,723 A | 4/1994 | Chenard |
| 5,866,537 A | 2/1999 | Bianchi |
| 6,104,956 A | 8/2000 | Naritoku et al. |
| 6,255,280 B1 | 7/2001 | Scheff |
| 8,952,040 B2 | 2/2015 | Yue et al. |
| 2019/0046486 A1* | 2/2019 | De Rienzo ........... A61K 31/198 |
| 2020/0163919 A1* | 5/2020 | Carroll ................. A61K 31/198 |

FOREIGN PATENT DOCUMENTS

| | | | | |
|---|---|---|---|---|
| WO | WO-2014172341 A1 * | 10/2014 | ........... | A61K 31/198 |
| WO | 2016112170 A1 | 7/2016 | | |

OTHER PUBLICATIONS

Aquilani et al. "Branched-Chain Amino Acids Enhance the Cognitive Recovery of Patients with Severe Traumatic Brain Injury". Arch Phys Med Rehabil. Sep. 2005; 86(9):1729-1735. (Year: 2005).*
Cole et al. "Dietary Branched Chain Amino Acids Ameliorate Injury-Induced Cognitive Impairment". Proc Natl Acad Sci USA. Jan. 5, 2010; 107(1):366-371. (Year: 2010).*
Marco A. Stefani et al. "Elevated glutamate and lactate predict brain death after severe head trauma" Annals of Clinical and Translational Neurology 2017; 4(6): 392-402.
Rejean M. Guerriero et al. "Glutamate and GABA imbalance following traumatic brain injury" Curr Neurol Neurosci Rep. Author manuscript; available in PMC May 1, 2016., pp. 1-20.
Roberto Aquilani, MD et al. "Branched-Chain Amino Acids May Improve Recovery From a Vegetative or Minimally Conscious State in Patients With Traumatic Brain Injury: A Pilot Study" Arch Phys Med Rehabil vol. 89, Sep. 2008, 1642-1647.
Bifari et al. "Branched-Chain Amino Acids Differently Modulate Catabolic and Anabolic States in Mammals: A Pharmacological Point of View". British Journal of Pharmacology. Jun. 2017; 174(11): 1366-1377. (Year: 2017).
Bonau M.D. et al, "High-Branched Chain Amino Acid Solutions: Relationship of Composition to Efficacy" Journal of Parenteral and Enteral Nutrition vol. 8, No. 6, Nov./Dec. 1984 pp. 622-627.
David O. Kennedy "B Vitamins and the Brain: Mechanisms, Dose and Efficacy—A Review" Nutrients 2016, 8, 68 pp. 1-29.
Ganesan et al, "Astroglial biotin deprivation under endoplasmic reticulum stress uncouples BCAA-mTORC1 role in lipid synthesis to prolong autophagy inhibition in the aging brain" Journal of Neurochemistry. 2020;154:562-575.
Khatri et al, "The Complexity of Secondary Cascade Consequent to Traumatic Brain Injury: Pathobiology and Potential Treatments" Current Neuropharmacology, 2021, vol. 19, No. 11, 1984-2011.
Lai et al, "Excitotoxicity and stroke: Identifying novel targets for neuroprotection" Progress in Neurobiology 115 (2014) 157-188.
Saleemani et al, "Determining ideal balance among branched-chain amino acids in medical formula for Propionic Acidemia: A proof of concept study in healthy children" Molecular Genetics and Metabolism 135 (2022) 56-62.
Stoppani et al, "Consuming a supplement containing branched-chain amino acids during a resistance-training program increases lean mass, muscle strength and fat loss" Journal of the International Society of Sports Nutrition 2009, 6 (Suppl 1):P1.

* cited by examiner

*Primary Examiner* — Jeffrey S Lundgren
*Assistant Examiner* — Michael J Schmitt
(74) *Attorney, Agent, or Firm* — Umberg Zipser LLP

(57) ABSTRACT

Compositions and methods are presented that, upon administration prior to trauma, are effective to prevent and/or reduce severity of sequelae of TBI upon trauma. Advantageously, the compositions presented herein can be orally administered, have an excellent safety profile, and will not require a prescription by physician or hospital admission.

16 Claims, 2 Drawing Sheets

COMPOSITIONS AND METHODS FOR PREVENTION AND REDUCTION OF TRAUMATIC BRAIN INJURY

This application is a continuation-in-part of copending U.S. patent application with the Ser. No. 17/572,368, filed Jan. 10, 2022, which claims priority to U.S. provisional patent application with the Ser. No. 63/137,507, filed Jan. 14, 2021, both of which are incorporated by reference herein.

FIELD OF THE INVENTION

The field of the invention is compositions and methods for prevention and reduction of traumatic brain injury, especially as it relates to neuroprotective use of branched chain amino acids and vitamins B and C before brain injury.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Traumatic brain injury (TBI) remains the most common cause of morbidity and mortality in adolescents and adults with approximately 13 million cases annually in the US and Europe. TBI has become the signature injury of the military conflict in Iraq and Afghanistan, and sports-related TBI accounts for over 4 million mostly mild cases in addition to the majority of mild concussions not even being reported. Individuals affected by TBI often experience numerous alterations in functional status, self-care ability, and cognitive, emotional, and social functioning.

Unfortunately, less than half of the patients suffering sports-related concussion recover within two weeks while most require up to 28 days for recovery. Indeed, a recent study on mild TBI demonstrated that patients can have elevated inflammatory cytokines up to 12 months after injury. Thus, early intervention for reversal of the pathobiochemical cascade is essential to halt or reverse damage and various attempts have been undertaken to treat TBI by pharmacological as well as non-pharmacological interventions.

For example, U.S. Pat. No. 6,104,956 teaches a non-pharmacological intervention in which TBI was treated using vagus nerve stimulation. In other examples, pharmacological interventions used one or more drugs that are preferably administered shortly after trauma as is described in U.S. Pat. No. 6,255,280 where effective amounts of cyclosporin A were administered to reduce lesion volume. In other attempts (e.g., WO 03/024458), a non-competitive AMPA receptor antagonist was described to treat TBI, and WO 97/17074 teaches use of various methylpyridines to improve cognitive performance and to attenuate injury-reduced reductions of cholinergic neurons in traumatic brain injury. In still other examples, U.S. Pat. No. 5,306,723 describes use of various neuroprotective indolone and related derivatives for treatment of TBI and other CNS disorders. Unfortunately, none of these treatment efforts have become an effective standard for TBI treatment for various reasons.

More recently, molecular events surrounding TBI have been elucidated, and the role of certain brain metabolites has gained significant attention. For example, significant glutamate and GABA imbalances following traumatic brain injury were consistently observed with TBI (see e.g., *Curr Neurol Neurosci Rep.* 2015 May; 15(5): 27) and elevated glutamate and lactate levels have been shown predict brain death after severe head trauma (see e.g., *Annals of Clinical and Translational Neurology* 2017; 4(6): 392-402). Moreover, it was overserved that the pathophysiology of TBI occurs in phases with a progressive cascade of events. The first step in this cascade occurs in the acute phase (less than one hour post trauma) and is characterized by an immediate and massive release of glutamate from the presynaptic terminals, which disrupts ionic equilibrium on postsynaptic membranes. Glutamate, being the major excitatory neurotransmitter, leads to rapid depolarization of postsynaptic membranes. The amount of glutamate released has been found to correlate with the severity of injury and with mortality. In addition, extracellular potassium release follows, which in turn depends on the initial release of glutamate. As extracellular potassium increases, intracellular calcium levels increase, leading to subsequent increases in mitochondrial calcium uptake. Excess mitochondrial calcium leads to oxidative stress, which impairs mitochondrial function and can lead to cellular death. Interestingly, accumulation of intracellular calcium has been correlated with cognitive dysfunction, and, as calcium levels drop, cognitive function improves.

Animal and human studies have both demonstrated beneficial effects of branched-chain amino acids (BCAA) after TBI. For example, it was demonstrated that providing BCAA in drinking water after TBI restored hippocampal levels of BCAA and improved cognitive function as compared to untreated TBI mice. Moreover, sham mice receiving BCAA did not show elevations in hippocampal BCAA levels suggesting that BCAA utilization in the brain may possibly be dependent on the brain's immediate need for BCAA.

A post-injury study in human reported circulating BCAA levels in healthy individuals and in patients having mild and severe TBI. Notably, it was found that BCAA levels were significantly lower in the TBI patients, and that lower BCAA levels correlated with the severity of TBI, possibly suggesting that BCAA were being utilized by the brain. A subsequent study performed on severe TBI patients provided a 19-gram daily dose of BCAA to 20 severe TBI patients and compared these patients to 20 age-matched and GCS-matched controls. Impressively, 68% of the BCAA-treated patients emerged from post-TBI vegetative states, while none of the untreated changed status (*Arch Phys Med Rehabil* Vol 89, September 2008, 1642-1647).

Unfortunately, while treatment of TBI post trauma has made considerable progress and alleviated at least some of the symptoms of TBI patients, there is currently no treatment available to prevent TBI and/or reduce severity of TBI prior to trauma. As will be readily recognized, such treatment would be highly desirable for individuals at risk for TBI such as military service members and participants in contact sports. Moreover, it would be desirable to have such treatments readily available and in a nutritionally acceptable format that will not require a physician or hospital visit/admission.

Thus, even though various compositions and methods of treatment of existing TBI are known in the art, all or almost all of them suffer from several drawbacks. Therefore, there remains a need for compositions and methods suitable to prevent TBI and/or reduce severity of TBI, especially where such compositions can be taken prophylactically without the need for prescription.

SUMMARY OF THE INVENTION

The inventive subject matter is directed to various compositions and methods of prophylactic neuroprotection that prevents or reduces sequelae of traumatic brain injury (TBI) where contemplated compositions are administered to a subject before the subject is at risk for TBI. Advantageously, the compositions presented herein can be orally administered have an excellent safety profile and can be provided in form of a sports drink or snack.

In one aspect of the inventive subject matter, the inventor contemplates a method of prophylactic neuroprotection that prevents or reduces sequelae of traumatic brain injury (TBI) that includes a step of orally administering to a subject in need thereof a composition that comprises branched chain amino acids (BCAA) and optionally a plurality of vitamins. Most typically, the branched chain amino acids include leucine, valine, and isoleucine, and especially contemplated vitamins include one or more of vitamin C, vitamin $B_3$, vitamin $B_5$, vitamin $B_6$, vitamin $B_7$, vitamin $B_9$, and vitamin $B_{12}$. It is further generally contemplated that the composition is administered before the subject is at risk for TBI.

In some embodiments, the leucine, valine, and isoleucine are present in the composition at a weight ratio of about 2:1:1 (e.g., in a total amount of about 7,000 mg per dosage unit). In further embodiments, the composition comprises at least two or at least four distinct vitamins, and most typically includes the vitamin C, the vitamin $B_3$, the vitamin $B_5$, the vitamin $B_6$, the vitamin $B_7$, the vitamin $B_9$, and the vitamin $B_{12}$. It is still further preferred that a dosage unit of the composition will not exceed the RDA (recommended daily allowance) for any one of the BCAAs and for most of the vitamins. While not limiting the inventive subject matter, it is also preferred that the composition is formulated as a beverage, a snack bar, or a ready-to-use powder, and may further include one or more minerals, carbohydrates, and/or an herbal extract (or components thereof).

Most typically, the composition is administered at least 15 minutes or at least 30 minutes before the subject is at risk for TBI. In still further exemplary embodiments, it should be recognized that the sequelae of TBI comprise cognitive and/or behavioral dysfunction, motor neural dysfunction (coordination) and/or vestibular dysfunction (balance), and/or cerebral inflammation and/or hyperglycemia. Still further, it is contemplated that at least one additional dosage unit of the composition may be administered upon the TBI in oral or parenteral fashion. Such further administration may be in quantity that is determined by a severity of the TBI and/or body weight of the subject. As will be readily appreciated, typical risks for TBI will include activities such as a contact sport activity, a motor sport activity, or a military engagement.

Therefore, the inventor also contemplates a neuroprotective composition that includes a nutritionally or a pharmaceutically acceptable carrier in combination with branched chain amino acids (BCAA) and optionally a plurality of vitamins, wherein the branched chain amino acids include leucine, valine, and isoleucine, and wherein the plurality of vitamins are selected from the group consisting of vitamin C, vitamin $B_3$, vitamin $B_5$, vitamin $B_6$, vitamin $B_7$, vitamin $B_9$, and vitamin $B_{12}$. The composition is preferably formulated such that a dosage unit, when administered to a subject before a TBI, prevents or reduces sequelae of TBI.

For example, the leucine, valine, and isoleucine may be present in the composition at a weight ratio of about 2:1:1 (e.g., in a total amount of about 7,000 mg per dosage unit). Most typically, contemplated compositions will comprises at least three distinct vitamins among the plurality of vitamins, and more preferably the vitamin C, the vitamin $B_3$, the vitamin $B_5$, the vitamin $B_6$, the vitamin $B_7$, the vitamin $B_9$, and the vitamin $B_{12}$. For example, the vitamin C may be present in an amount of about 200 mg, the vitamin $B_3$ may be present in an amount of about 16 mg, the vitamin $B_5$ may be present in an amount of about 5 mg, the vitamin $B_6$ may be present in an amount of about 10 mg, the vitamin $B_7$ may be present in an amount of about 30 mg, the vitamin $B_9$ may be present in an amount of about 400 mcg, and the vitamin $B_{12}$ may be present in an amount of about 50 mcg per dosage unit. Where desired, the composition may further comprise minerals, carbohydrates, and/or an herbal extract (or component thereof), and the composition may be associated with an instruction to administer the composition to a subject before the subject is at risk for TBI.

In certain embodiments, the composition is formulated as a beverage, a snack bar, or a ready-to-use powder, while in other embodiments the composition is formulated for parenteral administration. As noted before, it is contemplated that the sequelae of TBI may include cognitive and/or behavioral dysfunction, may include motor neural dysfunction (coordination) and/or vestibular dysfunction (balance), and/or may include cerebral inflammation and/or hyperglycemia.

Various objects, features, aspects, and advantages of the inventive subject matter will become more apparent from the following detailed description of preferred embodiments, along with the accompanying drawing figures in which like numerals represent like components.

DETAILED DESCRIPTION

The inventor has unexpectedly discovered that sequelae of TBI can be prophylactically prevented or reduced by administration of a composition that directly mitigates a cascade of events in the pathophysiology of TBI. More particularly, the inventor discovered that the compositions and methods presented herein will enable a subject's physiology to blunt TBI-induced glutamate flooding, and with that lessen associated adverse downstream effects in the brain, including oxidative stress, mitochondrial dysfunction, inflammation, and even cell death. Notably, these advantages can be achieved in a remarkably safe and effective manner that uses components common to ordinary human nutrition without the need for a prescription or hospital admission.

While the compositions and methods presented herein are primarily intended for prophylactic administration (i.e., before possible occurrence of a TBI), it should be recognized that the compositions and methods are also effective to enhance/shorten time to recovery once a TBI has occurred. Moreover, it should be recognized that treatment post-TBI can be continued with contemplated compositions via oral and/or parenteral route as is discussed in more detail below.

As used herein, the term "TBI" or "traumatic brain injury" refers to a condition in which the brain has been subjected to a rapid acceleration/deceleration, blast wave, and/or penetrating injury, which may be accompanied by loss of consciousness and/or retrograde amnesia. The Glasgow Coma Scale (GCS) classifies traumatic brain injuries as mild (14-15), moderate (9-13), or severe (3-8), and all TBIs falling in that range of scores are considered to fall within the scope of this disclosure.

While not wishing to be bound by any specific theory or hypothesis, the inventor contemplates that the compositions presented herein synergize to condition the physiology, and especially the brain physiology, into a state in which TBI-induced glutamate flooding is readily counterbalanced by a variety of factors, including: (1) acute and transient post-administration increase in available leucine along with supportive levels of isoleucine and valine to facilitate effective transamination reactions, (2) acute and transient post-administration increase in vitamins that act as enzymatic cofactors to facilitate effective regeneration of neurotransmitter synthesis, (3) acute and transient post-administration increase in vitamins that act as enzymatic cofactors to facilitate glucose metabolism and to reduce hyperglycemia, (4) acute and transient post-administration increase in vitamins that act as enzymatic cofactors to enable neuronal growth and tissue repair, and/or (5) acute and transient post-administration increase in vitamins that act as enzymatic cofactors to moderate oxidative stress and inflammation.

Figure 1:
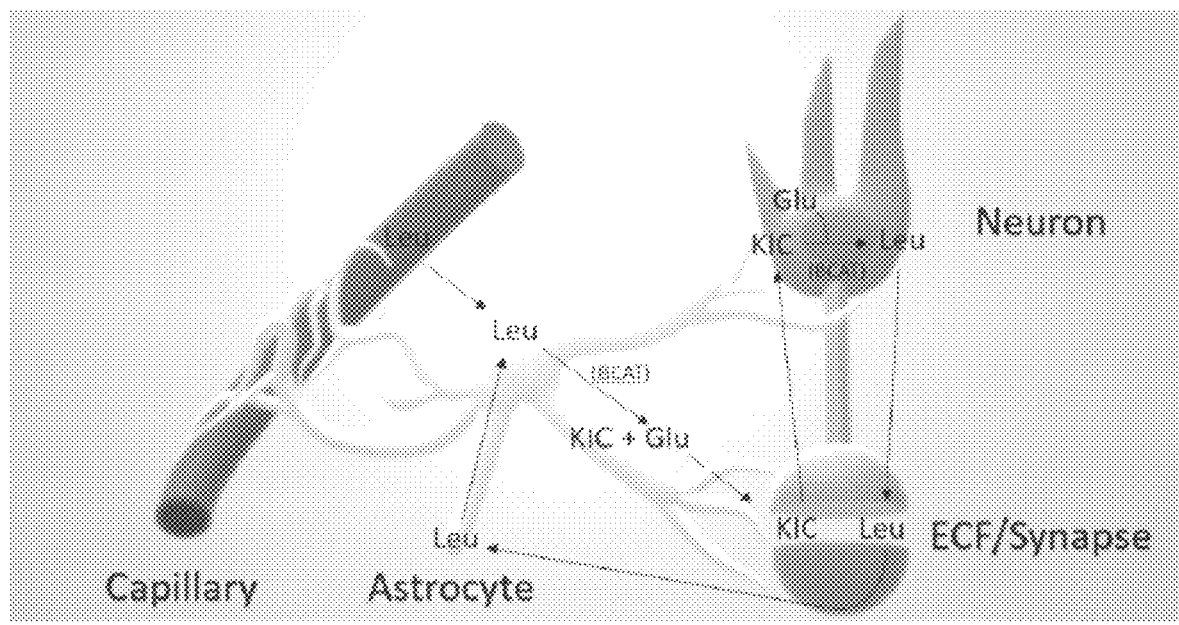
FIG. 1 is a schematic illustration of the leucine-glutamate cycle described herein.

In this regard, it should be recognized that leucine has a unique role in brain physiology in that leucine is the predominant nitrogen donor (responsible for at least 50% of the nitrogen supplied) in the synthesis of glutamate and glutamine from alpha-ketoglutarate within the brain. Leucine crosses the blood-brain barrier (BBB) faster than any other amino acid, first passing into astrocytes, where leucine is swiftly transaminated, giving rise to glutamate and glutamine, as well as a branched-chain μ-ketoacid (KIC, keto-isocaproic acid). KIC is not oxidized at the same rate as it is produced. Instead, it is released from astrocytes to neurons, which are capable of reversing the transamination process and reforming leucine, in the process consuming glutamate to so establish a "glutamate buffering system" when levels of these excitatory amino acids become excessive. Leucine formed in neurons can be released back to astrocytes, thereby constituting a "leucine-glutamate cycle" that, like the glutamate-glutamine cycle, serves to shuttle nitrogen between astrocytes and neurons as is exemplarily depicted in FIG. 1. In particular, FIG. 1 depicts the capillary-astrocyte-neuron interaction demonstrating the "leucine-glutamate cycle" in which leucine crosses the blood-brain barrier where it is converted via branched-chain amino acid transferase (BCAT) into keto-isocaproic acid (KIC) to form glutamate from alpha-ketoglutarate. The astrocyte then releases KIC to the neuron where it is reverse transaminated back to leucine, in the process consuming glutamate and thus providing a buffering for excess glutamate and halting a TBI-induced glutamate-based pathobiochemical cascade. As will be readily appreciated, leucine plays a central role in such mechanism. However, under normal physiological conditions, the quantity of leucine is insufficient to absorb TB-induced glutamate release.

In addition to the important role of leucine, it should be appreciated that as branched chain amino acids are essential amino acids, the body has no mechanism for de novo synthesis and must therefore rely on dietary sources and/or interconversion from other metabolites. A rapid depletion of leucine under TBI glutamate flooding would, unless mitigated, lead to a rapid imbalance of leucine:isoleucine:valine, which may have further adverse effect of brain physiology. Therefore, the inventor contemplates that leucine should not be given alone, but preferably be delivered in an approximate 2:1:1 ratio of leucine:isoleucine:valine to avoid disrupting the temporal pattern. Notably, and as is shown in more detail below, absorption of BCAA (as well as of B-vitamins and vitamin C) upon oral delivery is rapid, and in view of the above and favorable oral bioavailability, the inventor contemplates various compositions and methods for prophylactic neuroprotection that prevent or reduce sequelae of TBI. Preferably, such compositions are at least initially orally administered before occurrence of a TBI.

Therefore, in one exemplary embodiment, the inventor contemplates a composition that is formulated for oral administration such that one unit dosage provides the BCAA in quantities as noted in Table 1 below. As can be seen from the table approximate preferred amounts (+/−10%) will result in a formulation in which about 7,260 mg are provided while on the lower end of the alternate range about 4,455 mg and on the higher end of the alternate range 10,550 mg are provided in a single dosage unit.

TABLE 1

| Component | Preferred Amount (approximate) | Alternate Range (approximate) |
|---|---|---|
| Leucine | 3500 mg | 2000-5000 mg |
| Isoleucine | 1750 mg | 1200-2500 mg |
| Valine | 1750 mg | 1200-2500 mg |
| Vitamin C | 200 mg | 50-500 mg |
| Vitamin B3 | 16 mg | 5-50 mg |
| Vitamin B5 | 5 mg | 0.5-25 mg |
| Vitamin B6 | 10 mg | 1-50 mg |
| Vitamin B7 | 30 mg | 3-150 mg |
| Vitamin B9 | 400 mcg | 80-1000 mcg |
| Vitamin B12 | 50 mcg | 5-250 mcg |

Most typically, a dosage unit will be an individual serving such as a serving of an individually packaged beverage (e.g., sports drink or a hydration drink, or a mineral drink with total volume of 250-500 mL, or ready to use energy drink with total volume of 5-25 mL), a defined scoop of a powder (e.g., holding between 5 and 25 g of the dry composition), or a single serve snack item (e.g., as an energy bar weighing about 20-50 g). As will be readily appreciated, contemplated compositions can be formulated into any number and types of formats so long as such format is edible or drinkable, includes a nutritionally or pharmaceutically acceptable carrier, and contains at least 10%, or at least 20%, or at least 30%, or at least 40%, or at least 50% of a dosage unit of contemplated compositions. Therefore, consumption of 1-5 drinkable or edible units will provide at least one dosage unit of contemplated compounds.

With regard to contemplated quantities of the various components, it should be noted that the preferred amounts in Table 1 will fall well within the respective recommended daily allowance (RDA) for the components: leucine fulfills 93% of RDA, isoleucine fulfills 100% of the RDA and maintains the 2:1:1 suggested ratio of Leucine to isoleucine/valine, and valine fulfills 81% of the RDA while maintaining the 2:1:1 ratio.

With regard to the vitamin components and their role, it is noted that vitamin C is used for reduction of oxidative stress in TBI and has been recommended post-TBI to mitigate secondary brain injury. Preferred amounts in Table 1 is about >200% of RDA, but the tolerable upper intake dose per NIH guidelines is 2000 mg/day.

Vitamin $B_3$ (Niacin) is used for reduction of oxidative stress and modulates inflammatory reactions which occur in TBI. The preferred amount in Table 1 is 100% of RDA, and the safe upper consumption limit is 35 mg based on its ability to cause skin flushing at doses greater than 100 mg/day. Vitamin $B_5$ (Pantothenic acid) is generally required for oxidative metabolism as well as amino acid, cholesterol and neurotransmitter synthesis, and the preferred amount in Table 1 is 100% of RDA.

Vitamin $B_6$ (Pyridoxine) is a necessary cofactor for amino acid metabolism and synthesis of neurotransmitters including GABA. Indeed, the Branched-Chain Aminotransferase BCAT is dependent on $B_6$, and a deficiency leads to down-regulation of GABA and serotonin synthesis leading to removal of the inhibitory effects of GABA, thus allowing a hyperexcitability state of excess Glutamate. The preferred amount in Table 1 is 750% of 1.3 mg RDA. However, the upper consumption limit is at about 100 mg/day based on its ability to cause reversible sensory neuropathy at daily doses over 1000 mg/day for long periods.

Vitamin $B_7$ (Biotin) plays a key role in glucose metabolism within the brain, and as noted above, hyperglycemia occurs in the initial state of TBI and can continue for weeks. The preferred in Table 1 amount is 100% of RDA. B9 (Folate) is used for DNA/RNA synthesis and repair, as well as protein synthesis within the brain. B9 typically works in concert with vitamin $B_{12}$. The preferred in Table 1 amount is 100% of RDA. However, the upper consumption limit is at about 1000 mcg due to its ability at high doses to mask vitamin $B_{12}$ deficiency. Vitamin $B_{12}$ (Cyanocobalamin) works in concert with folate and is essential in rapidly developing tissue such as fetal neuronal growth or in brain injury/repair. The preferred amount in Table 1 is 2000% of RDA.

In this context, it is noteworthy that only three ($B_3$, $B_6$, $B_9$) of the above B vitamins have been ascribed a daily upper limit of consumption with the remainder being safe at any dose. Therefore, even where three dosage units would be administered, only B9 would be slightly above (200 mcg) the daily recommended dose.

Notwithstanding the preferred amounts and ranges in Table 1 it should be appreciated that contemplated compositions may vary considerably and that one or more of the components may be optional or be included in quantities outside those listed in Table 1. For example, where an individual already consumes a multivitamin, one or more of the vitamins may be omitted. In other examples, where an individual has a poor diet, quantities for one or more of the vitamins may exceed RDA by at least 10%, or by at least 50%, or by at least 100%, or by at least 200%, and even more.

Likewise, while the weight ratio of leucine:isoleucine:valine is preferably about 2:1:1 it should be noted that the BCAA can be included in other weight ratios, and contemplated weight ratios include those where each of the three BCAA are supplemented in equal quantities, or where one or two of the three BCAA may be present in an excess of at least 1.5-fold, or at least 2-fold, or at least 2.5-fold, or at least 3.0-fold, and even higher. Moreover, in at least certain embodiments, leucine may be administered as the only BCAA, or in combination with only one other BCAA (i.e., isoleucine or valine).

Additionally, it should be recognized that contemplated compositions may include additional (preferably functional) ingredients that may provide a desirable effect such as an antioxidant effect, metabolic support, cell and tissue repair support, and/or anti-inflammatory action. Therefore, suitable additional ingredients include minerals, carbohydrates, and/or herbal extracts (or individual components thereof).

In still further preferred embodiments, and based on the suspected mechanism of action, the inventor therefore contemplates that the compositions presented herein will be administered to an individual before a TBI occurs. Consequently, such administration is prophylactic and typically preferred with individuals that may be at risk for a TBI. Most commonly, such risk is associated with sports (e.g., soccer, basketball, water polo, etc.), and especially contact sports (e.g., football, rugby, martial arts, hockey, etc.), automotive racing, but also recreational activities associated with a higher fall risk such as (motor)cycling, skating, etc. In addition, it is contemplated that military service personnel in combat situations and/or hostile territory will also be at increased risk for TBI and blast-TBI. Regardless of the particular risk situation, it is generally preferred that the compositions presented herein will be administered in the quantities as noted above, and most preferably in the quantities as shown in Table 1. Most typically, to allow absorption into the circulatory system and cerebrospinal fluid, oral administration of the inventive compositions be at least 10 minutes, or at least 20 minutes, or at least 30 minutes or at least 40 minutes in advance of a situation where TBI risk is increased.

However, it is contemplated that contemplated compositions may also be provided to an individual upon a suffering a TBI, and that administration is preferably oral administration using the same compositions as presented herein. Nevertheless, in further contemplated aspects, post-TBI administration may also be via parenteral administration, and most preferably by intravenous infusion. In such case, it is contemplated that the formulation may be 'fine-tuned' to the specific degree of severity as evaluated by GCS score and/or to the specific body weight of the patient. Therefore, the inventor also specifically contemplates liquid compositions that are formulated for injection/infusion. Most typically, the quantities of ingredients will be within the range of those presented in Table 1 above.

For example, based on human absorption and metabolic studies (see below), it is contemplated that an athletes participating in contact sports may ingest an approximate 7 gram dose of the BCAA composition about 20-30 minutes before a game or practice, and if the athlete suffers a concussion, he/she should immediately take another 7 gram dose and remain on 14-21 gram doses a day (7 gram dose 2-3 times a day) for 7-10 days.

Therefore, it should be appreciated that the compositions and methods presented herein will prevent or reduce one or more sequelae of TBI, and especially contemplated sequalae include cognitive dysfunction (e.g., confusion, loss of attention, memory, recall, executive function, etc.), behavioral dysfunction (e.g., depression, anxiety, moodiness, etc.), motor neural dysfunction (e.g., weakness, loss in body coordination or controlled movement, etc.), vestibular dysfunction (e.g., loss or impairment of balance), seizures, pain (especially headache), cerebral inflammation, and/or hyperglycemia (systemic or cerebral). Moreover, and as is also described in more detail below, contemplated compositions also reduce or even prevent pathological changes in the brain, and especially the temporal lobe.

EXAMPLES

The following examples are provided to give exemplary guidance to a person of skill in the art and are not intended to be limiting to the inventive subject matter. To that end, the inventor performed a number of studies to demonstrate the neuroprotective and restorative effects of contemplated compositions on the sequelae of TBI. Underlying the investigation was the hypothesis that if BCAA (and vitamins) were elevated in the circulation prior to a TBI, the brain could readily access the BCAA (and vitamins) and the severity of injury would be reduced.

Methods: A standard weight-drop method was used on 50 adult mice to model a closed-head TBI in humans. The mice were randomized into groups that were shams, untreated, and pre-treated, post-treated or pre+post-treated with BCAA. Pretreated mice received BCAA through supplemented water and were dosed via oral gavage 45 mins prior to TBI induction. All mice underwent beam walking to assess motor recovery and Morris water maze assessed cognitive function post-injury.

Expected Outcomes: Pre-treated and Pre+post-treated mice exhibited significantly better motor recovery and cognitive function than the other groups. The pre+posttreated group performed the best overall while the post-treated group only improved in memory after day 7 of the study.
Methods Animals: Adult female C57BL/6J mice were obtained from Jackson Labs, Inc. (Bar Harbor, ME) and housed in groups of 5 on a 12 h:12 h light schedule with ad libitum access to chow and water throughout the study. The ordering and receipt of the animals were coordinated with the study design that called for 3 days of pretreatment before injury and a standard injury weight of 20±0.5 grams. All animals were between 84-91 days of age at the time of injury. All animal procedures were approved by the Institutional Animal Care and Use Committee at Inotiv-Boulder, Inc.

Study Design. Plasma Leucine Levels. A pilot study was used to determine peak plasma leucine levels in these mice at baseline and at 30, 45, 90 and 120 minutes after a single oral gavage dose of BCAA (isoleucine, 168 mg/kg; leucine, 335 mg/kg; valine, 168 mg/kg; 20 ml/kg dose volume). Dosing was based on an equivalent human dose of 21 gms of BCAA 2:1:1 ratio. Leucine levels were measured via liquid chromatography/mass spectroscopy and levels peaked at 45 minutes after dosing.

The treatments (ad libitum water or ad libitum water supplemented with BCAA [isoleucine, 1.25 g/kg/d; leucine, 2.5 g/kg/d; valine, 1.25 g/kg/d]) were provided for 3 days prior to a sham procedure or traumatic brain injury (see below). In accordance with the predetermined plasma absorption profile of leucine after oral gavage 45 minutes directly before sham or TBI induction all animals received either water or water supplemented with BCAA (isoleucine, 168 mg/kg; leucine, 335 mg/kg; valine, 168 mg/kg; 20 ml/kg dose volume) via oral gavage. Directly after sham or TBI induction, the animals were either maintained on a water alone (sham or TBI), switched to water alone (Preinjury BCAA; Pre), or switched to BCAA-supplemented water (Postinjury BCAA; Post and Pre+Post) at the doses described above for ad libitum administration. The animals were randomized to the groupings by weight, and the researchers were blinded from the treatments throughout all experimental procedures.

Weight-Drop Injury: Fifty mice were anesthetized with 2.5% isoflurane delivered for 2 min. They were then placed individually in the prone position on a foam bed with their heads directly under a Plexiglas tube. A brass weight (80 g) was dropped once through the tube from a 0.8 m, striking the head directly and resulting in a closed-head injury. Animals were moved directly after being struck by the weight so that no secondary impacts occurred. They were then provided buprenorphine (0.1 mg/kg SC) directly after injury. Sham-injured mice underwent the same procedure, but the weight was not released. Injured mice had righting reflex recovery times >2 min, and the injury severities were comparable amongst all brain-injured groups. Sham-injured mice recovered the righting reflex at 24.3±4.8 sec. Mice were placed in a heated recovery cage and monitored until ambulatory (approximately 5 to 15 min) before being returned to their cage.

Beam Walking: A narrow wooden beam (5-mm wide× 100-mm long) was suspended 1 m above the ground with a goal box at the end. The animal was placed on the beam and the number of foot-faults for the right hindlimb was recorded over 50 steps. A baseline level of performance was achieved following 3 days of training (4 trials per day) prior to TBI, and animals were tested at 1 and 3 days post-TBI (1 trial each day) to assess acute motor recovery.

Morris Water Maze: Spatial learning ability was assessed in all mice 4 days after TBI induction. On days 4-11 after injury or sham, the mice were trained with 4 trials per day and a 15-min inter-trial interval. Mice started from one of the four pool quadrants, and the starting point was varied for each animal and each testing day. If an animal did not find the platform within 60 sec during a given trial, it was placed on the platform for 10 sec by the handler. Four hours following the last acquisition trial, the platform was removed and a 60-sec retention trial was performed. Twenty-four hours following the last acquisition trial, the platform was removed and a 60-sec, longer-term retention trial was performed. Every trial was recorded and analyzed with EthoVision (Noldus Inc., Wageningen, the Netherlands).

Figure 2:
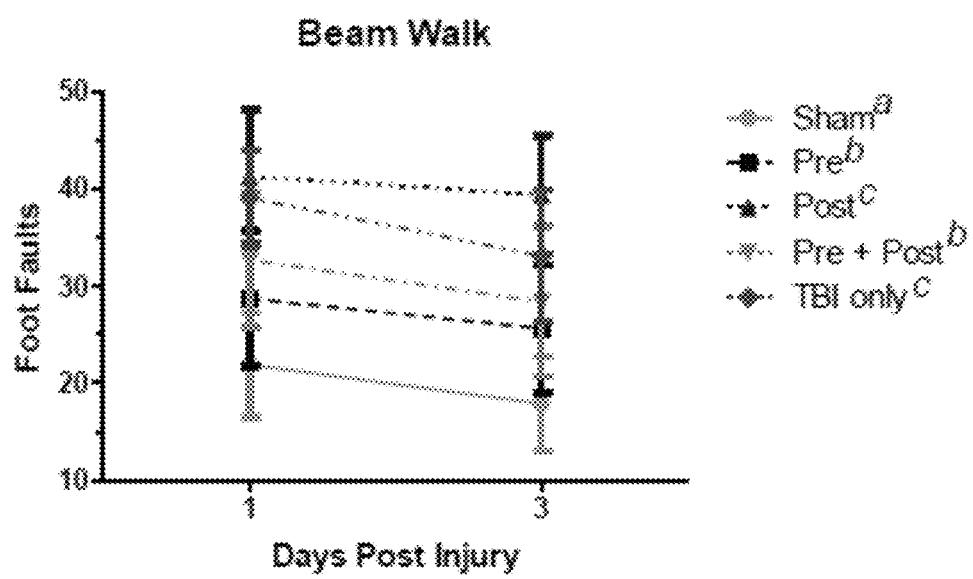
FIG. 2 is a graph depicting exemplary results for a beam walking test for mice following TBI and treatment with various protocols.

Statistics: Groups were compared using one-way analysis of variance (ANOVA) or one-way repeated measures ANOVA (RMANOVA) followed by Tukey's post hoc tests to determine group differences. Significance for all tests was set at $p<0.05$. All graphing and statistical tests were performed with GraphPad Prism v5.0 (GraphPad; San Diego, CA).
Results Acute Motor Recovery: FIG. 2 shows that BCAA pretreatment was necessary to improve performance in the beam walking task after TBI on post-injury days 1 and 3. One-way RMANOVA detected a main effect of treatment $[F_{(1,4)}=107.9, p<0.001]$, while Tukey's post hoc test indicated that Pre- and Pre+Post-treated animals had significantly fewer foot faults than untreated TBI animals and animals treated only after TBI. As can be seen from FIG. 2, pretreatment with BCAA improved acute motor recovery after TBI. Animals provided BCAA before the injury (Pre and Pre+Post) had better beam walking performance than untreated animals and animals given BCAA after the injury alone (Post). Error bars represent the SEM. Groups that do not share common letter designations differed significantly in Tukey's post hoc test.

Spatial Learning and Memory: The latency to find the submerged platform in the Morris water maze was measured to assess spatial learning acquisition on days 4-11 post-injury. As FIG. 3A illustrates, one-way RMANOVA detected a main effect of treatment [$F_{(4,28)}=12.17$, $p<0.001$)], and, over the course of the task training, the sham, pretreated, and pre+post-treated groups found the platform significantly faster than the untreated TBI group and the animals that received post-treatment alone.

Figure 3:
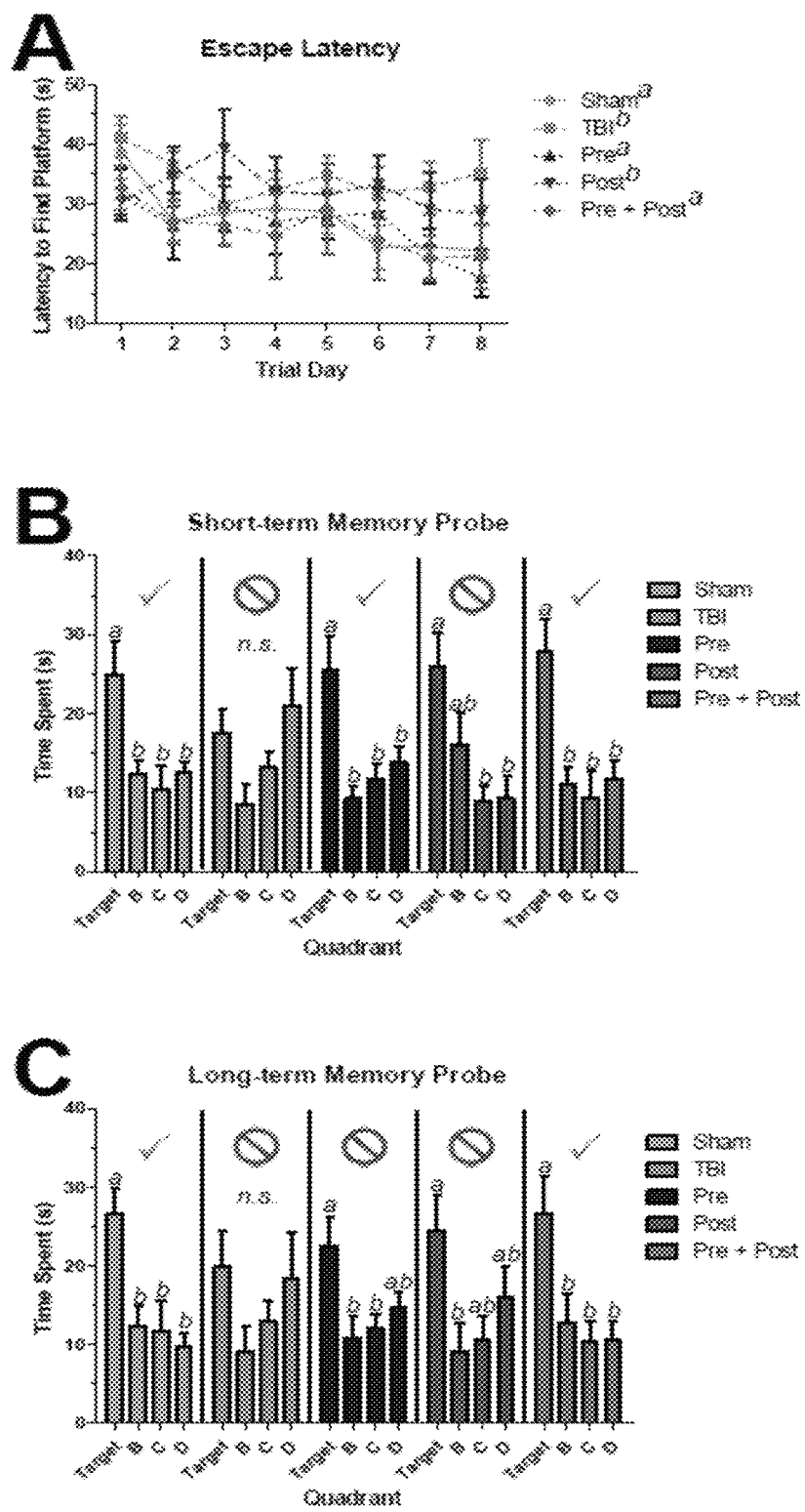
FIG. 3 is a graph depicting exemplary results for spatial learning and memory of mice following TBI and treatment with various protocols.

The same group differences persisted in the short-term memory probe trials when the escape platform was removed (FIG. 3B). The shams, pretreated animals, and pre+post-treated animals were able to differentiate the target quadrant of the maze from all other maze quadrants (green checkmarks) as assessed by one-way ANOVA followed by Tukey's post hoc test. In contrast, the untreated TBI group could not differentiate any of the quadrants, while the post-treated group had some memory but could only differentiate quadrants on the opposite side of the maze (quadrants C & D) from the target quadrant (red not symbols). The statistical parameters were as follows: shams, [$F_{(3,24)}=5.30$, $p=0.006$)]; untreated TBI, not significant; pretreated, [$F_{(3,24)}=6.70$, $p=0.002$)]; post-treated, [$F_{(3,24)}=5.52$, $p=0.005$)]; pre+post-treated, [$F_{(3,24)}=7.96$, $p<0.001$)].

FIG. 3C shows that the results of the long-term memory probe trials were similar to those of the short-term probes, but the pretreated animals did not perform as well. Only the shams and pre+post-treated animals differentiated the target quadrant from all of the others, while the pretreated animals and the post-treated animals could tell the difference between the target and only 2 of the 3 non-target quadrants. Again, the untreated TBI group had no preference for any particular quadrant. The statistical parameters were as follows: shams, [$F_{(3,24)}=6.77$, $p=0.002$)]; untreated TBI, not significant; pretreated, [$F_{(3,24)}=4.16$, $p=0.017$)]; post-treated, [$F_{(3,24)}=3.22$, $p=0.040$)]; pre+post-treated, [$F_{(3,24)}=5.02$, $p=0.008$)].

As can be taken from the results in FIG. 3A-C, Pretreatment with BCAA improved spatial learning and memory after TBI better than post-treatment alone. A) Animals provided BCAA before the injury (Pre and Pre+Post) had better task learning in the Morris water maze than untreated animals and animals given BCAA after the injury alone (Post). B) Animals provided BCAA before the injury (Pre and Pre+Post) remembered the location of the escape platform in a short-term memory task more effectively than untreated animals and animals given BCAA after the injury alone (Post). C) Animals provided BCAA both before and after brain injury (Pre+Post) remembered the location of the escape platform in a long-term memory task more effectively than untreated animals (TBI), pretreated animals (Pre), and animals given BCAA after the injury alone (Post). Error bars represent the SEM. Data sets that do not share common letter designations differed significantly in Tukey's post hoc test.

Neuropathology: Results demonstrated that mice who ingested a 21 gram BCAA dose 30 mins prior to a standardized moderate traumatic brain injury similar to the protocol above had statistically significant ($P<0.01$) less brain damage when looking at the temporal lobes, the motor cortex and the hippocampus. Notably, significantly less tissue damage was observed in all three groups of treated mice: the pretreatment group, the pre/posttreatment group, and the posttreatment group. Therefore, the overall results of the neuropathological analysis correlated with the clinical findings supporting the conclusions that pretreatment with BCAA's provides a significant neuroprotective effect as well as neurorestorative.

Absorption in human after oral administration—Human metabolic study using one dose 7 gram of the composition as shown in Table 1. Six adult subjects were randomly selected for participation. Each subject had Leucine, Isoleucine and Valine (BCAA) levels drawn at baseline. The subjects then ingested a 7 gram dose of the composition as shown in Table 1, waited 30 minutes and had BCAAs' recollected to assess changes in levels. Results: Valine increased 3.5x, Isoleucine increased 5.1x, leucine increased 7.6x. As can be readily seen, the BCAA were rapidly included into the systemic circulation (and cerebrospinal fluid from there) and clearly indicate the significant utility in methods of prophylactic neuroprotection that prevent or reduce sequelae of TBI.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other)

and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of prophylactic neuroprotection that prevents or reduces at least one sequelae of traumatic brain injury (TBI), comprising:
   orally administering to a subject about to engage in an activity selected from a contact sport, a motor sport, and a military engagement a composition that comprises a branched chain amino acids (BCAA) component and a vitamin component at least 10 minutes prior to participating in the activity;
   wherein the BCAA component comprises leucine, valine, and isoleucine, and wherein the leucine, the valine, and the isoleucine are present in the BCAA component at a weight ratio of X:1:1, with X being between 2-4;
   wherein the vitamin component comprises vitamin $B_7$ and at least one vitamin selected from the group consisting of vitamin C, vitamin $B_3$, vitamin $B_5$, vitamin $B_6$, vitamin $B_9$, and vitamin $B_{12}$; and
   wherein the sequelae of TBI are selected from cognitive dysfunction, behavioral dysfunction, motor neural dysfunction, vestibular dysfunction, cerebral inflammation, and hyperglycemia.

2. The method of claim 1, wherein the composition comprises at least three vitamins selected from said group.

3. The method of claim 1, wherein the composition comprises the vitamin C, the vitamin $B_3$, the vitamin $B_5$, the vitamin $B_6$, the vitamin $B_7$, the vitamin $B_9$, and the vitamin $B_{12}$.

4. The method of claim 1, wherein the BCAA component is present in the composition in an amount of 10,000 mg+/−10%.

5. The method of claim 1, wherein the composition is formulated as a beverage, a snack bar, or a ready-to-use powder and wherein the composition optionally further comprises minerals, carbohydrates, and/or an herbal extract.

6. The method of claim 1, wherein the composition is administered at least 15 minutes prior to participating in the activity.

7. The method of claim 1, wherein the BCAA component is administered in an amount of between 4,400 mg and 10,000 mg.

8. The method of claim 1, wherein the vitamin $B_7$ component is administered in an amount of between 3-150 mg.

9. The method of claim 1, further comprising orally administering at least one additional dosage unit of the composition upon the TBI.

10. The method of claim 1, further comprising parenterally administering the composition upon the TBI.

11. The method of claim 1, wherein the activity is a contact sport.

12. The method of claim 1, wherein the composition comprises the vitamin C, the vitamin $B_3$, the vitamin $B_5$, the vitamin $B_6$, the vitamin $B_7$, the vitamin $B_9$, and the vitamin $B_{12}$.

13. The method of claim 1, wherein the BCAA component is present in the composition in an amount of 10,000 mg+/−10%.

14. The method of claim 12, wherein the BCAA component is present in the composition in an amount of 10,000 mg+/−10%.

15. The method of claim 13, comprising orally administering said composition 10-40 minutes prior to participating in the activity.

16. The method of claim 14, comprising orally administering said composition 10-40 minutes prior to participating in the activity.

* * * * *